United States Patent
Stamler

[19]

[11] Patent Number: 5,860,947
[45] Date of Patent: Jan. 19, 1999

[54] WOUND IRRIGATION DEVICE AND METHOD

[76] Inventor: Keith D. Stamler, P.O. Box 4375 Palos Verdes, Peninsula, Calif. 90274

[21] Appl. No.: 914,965

[22] Filed: Aug. 20, 1997

[51] Int. Cl.⁶ .................................................. A61M 1/00
[52] U.S. Cl. ............................ 604/19; 604/247; 604/290; 604/311
[58] Field of Search ................................ 604/19, 36–39, 604/28, 30, 246, 247, 248, 289, 290, 305, 310, 311, 150–152, 183–187

[56] References Cited

U.S. PATENT DOCUMENTS

| | | | |
|---|---|---|---|
| 4,747,834 | 5/1988 | Prindle | 604/184 X |
| 4,769,003 | 9/1988 | Stamler | 604/39 |
| 4,838,866 | 6/1989 | Marshall, Sr. | 604/152 |
| 5,224,940 | 7/1993 | Dann et al. | 604/290 |
| 5,254,092 | 10/1993 | Polyak | 604/247 X |
| 5,685,851 | 11/1997 | Murphy et al. | 604/150 |

*Primary Examiner*—John D. Yasko
*Attorney, Agent, or Firm*—Fulwider Patton Lee & Utecht, LLP

[57] ABSTRACT

A device for irrigating a wound wherein a syringe fitted with a two-way check valve is filled via a short fill stem that is dipped into irrigant contained in a basin and expelled through a discharge port. The use of a basin allows the irrigant to be positioned immediately adjacent the wound to minimize movement and allows the irrigant to be drawn into the syringe with minimal effort and concentration. The short fill stem minimizes pressure drop and allows the irrigant to be drawn into the syringe as quickly as possible.

8 Claims, 2 Drawing Sheets

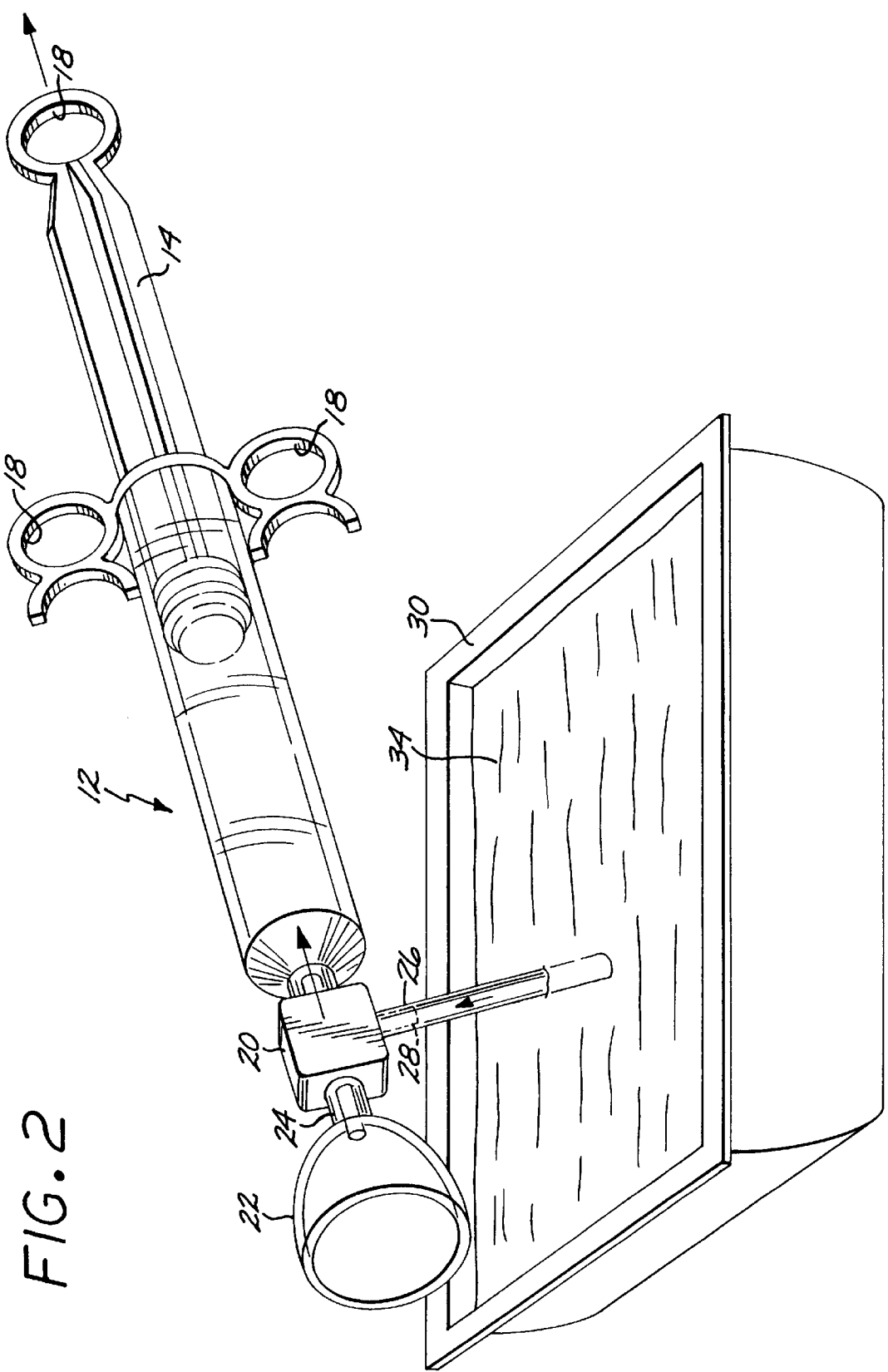

WOUND IRRIGATION DEVICE AND METHOD

BACKGROUND OF THE INVENTION

The present invention relates to the irrigation of wounds, and more particularly pertains to a device and method that enables a user to quickly, safely, and economically flush a wound with large volumes of irrigant.

In the medical profession lacerations, cuts, abrasions, puncture wounds, and the like are commonly irrigated to remove foreign debris such as road particles, dirt, bacteria, and other contaminants which could predispose to infection. Removal of these contaminants as well as blood which continually emanates from the wound and surrounding tissue is also required to provide the treating medical personnel a clear view of underlying tissue and other vital structures affected by the injury during the exploratory phase of treatment. Wound cleansing is again required prior to wound closure to avoid future medical complications caused by wound contamination.

A number of different devices and associated methods of wound irrigation have been in common use by medical personnel in clinics and emergency rooms as well as in the field. A syringe is commonly employed to direct liquid irrigant at the wound site to thereby impact the wound and mechanically dislodge undesired bacteria and foreign matter from the wound surface and surrounding tissue.

Medical personnel have the option of simply resorting to the use of a syringe and hypodermic needle combination. While the use of such a combination enables a stream of irrigant to be precisely aimed, the technique suffers from a number of shortcomings. Bloody irrigant reflecting off of the patient may contaminate the surrounding area and may pass infection to the irrigator or to other individuals in the immediate vicinity. Moreover, use of sharp instruments always poses the risk of injury, both to the patient as well as to personnel handling the needles, the latter further running the risk of contracting a disease the patient may be infected with. Additionally, in order to expedite the filling process, it is necessary to remove the hypodermic needle each time the syringe is to be refilled.

Another method of wound irrigation utilizes a device which offers several safety advantages over the syringe and needle combination. This irrigation device eliminates the use of a hypodermic needle and minimizes the possibility of disease transmission through rebounding irrigation spray by incorporating a splashback shield as described in U.S. Pat. No. 4,769,003 to Stamler which is incorporated herein by reference. A generally bell-shaped splashback shield which is removably attached to a hypodermic syringe functions to prevent potentially contaminated irrigation fluid from ricocheting off of the wound back towards the irrigator or other nearby personnel. Thus reflected fluids will be restrained by the shield, rather than splash onto and infect surrounding personnel. The shield incorporates an integral, thin-walled, hollow tubule which is capable of engaging a Luer-lock syringe tip. By virtue of the smaller diameter of the tubule relative to the syringe, exiting irrigation fluid forms a narrow irrigation stream which travels down the central longitudinal axis of the shield to impact the wound. While this device provides several safety advantages to the attending medical personnel, repetitive wound irrigation still remains a laborious task as the splashback shield must be removed in order to enable the syringe to be refilled. Similar to the previously described method of wound irrigation, repetitive irrigations require painstaking manipulation of the irrigation device to refill the syringe in preparation for each subsequent irrigation.

Many medical authorities suggest that all wounds require a minimum of 250 cc's of irrigation fluid to ensure proper cleansing of the injured area and surrounding tissue. Following this principle, large, heavily contaminated wounds require even larger volumes of irrigation. To accomplish this with common syringes capable of containing 10–20 cc's of fluid, multiple irrigations are required. Unfortunately the devices described above require the removal of either a hypodermic needle or splashback shield prior to each refilling of the syringe for subsequent irrigations. This functional requirement is both time consuming and adds undesirable complication to methods of wound irrigation utilizing these devices.

Wound irrigation devices are available wherein the above-described refilling problems are addressed. Such devices provide a syringe that is linked to an IV bag via a tube, usually 6' long. A valve fitted to the syringe allows irrigant from the IV bag to be drawn into the syringe upon extension of the plunger and expelled upon compression of the plunger. A spring is usually employed to assist in extending the plunger and a splashshield may be fitted to the syringe.

A number of shortcomings nonetheless become apparent upon using such devices, all a direct result of the saline solution being supplied from an IV bag. Because both the syringe as well as the 6' of tubing extending to the IV bag are initially empty, the system must first be primed with irrigant solution which requires the repeated extension and retractions of the plunger before a wound can be irrigated. Another disadvantage of this method of wound irrigation results from the length of flexible tubing suspended between the syringe and the IV bag containing the irrigant solution . It will be appreciated that the length of flexible tubing, extending from the IV bag to the syringe limits the user's range of motion during wound irrigation and is awkwardly present in the injured area. When the IV bag is located in close proximity to the irrigation site, the excess length of tubing becomes a potential distraction to the irrigator. As the irrigator moves relative to patient and as the syringe is repositioned about the wound site, attention must be given to any excess length of tubing to ensure that it remains clear of the treatment area. Furthermore, the length of tubing through which the irrigant must be drawn each time the syringe is filled also poses a substantial resistance to flow which not only requires a substantial effort to be expended but significantly retards the rate of flow and thereby slows down the whole process. Increasing the force provided by an assist spring is of limited value as such force must then be overcome when the plunger is compressed. Finally, because an IV bag cannot re resealed once accessed, its entire contents must be used or discarded. The need for only a few hundred cc's of irrigant would therefore result in a substantial amount of waste. Saline solution supplied in IV bags is also more expensive than when supplied in bottles.

Thus, there exists a need for a wound irrigation device that enables substantial volumes of irrigant solution to be directed at a wound as quickly as possible with minimal effort, inconvenience, and expense.

SUMMARY OF THE INVENTION

The present invention provides a wound irrigation kit and method of use which overcomes the shortcomings of the previously known devices and methods to enable a user to more quickly, easily, and inexpensively irrigate a wound.

The kit includes a syringe, optionally fitted with a splashback shield, in combination with a valve and a short fill tube for use with an open-faced basin. The valve is configured to cause fluid to be expelled upon compression of the plunger and drawn in through the fill tube upon extension of the plunger. The basin filled with irrigant solution allows the fill tube to be simply dipped thereinto during the filling operation. Such system, sans the supply bag, the support rack and the many feet of tubing associated with an IV-type system allows the syringe to be refilled with short swift movements that enables substantial volumes of irrigant to be directed at a wound in a much shorter period of time than had heretofore been possible. Additionally, such method saves on irrigant solution as only the amount needed for a particular size wound may be poured into the basin from a reclosable bottle of inexpensive irrigation solution while the entire contents of an IV bag must either be used or discarded once a bag has been accessed using other devices.

These and other features and advantages of the present invention will become apparent from the following detailed description of a preferred embodiment which, taken in conjunction with the accompanying drawings, illustrates by way of example the principles of the invention.

BRIEF DESCRIPTION OF THE DRAWINGS

FIG. 2 is a perspective view of the wound irrigation device being filled in accordance with the present invention.

DETAILED DESCRIPTION OF A PREFERRED EMBODIMENT

The drawings generally illustrate the components of the wound irrigation kit of the present invention. The kit is used to flush debris, blood and contaminants from a wound to prevent infection, enable any necessary repairs to be made and facilitate healing. The kit is easy and convenient to use and allows irrigant to be delivered much more quickly than has heretofore been possible.

Figure 1:
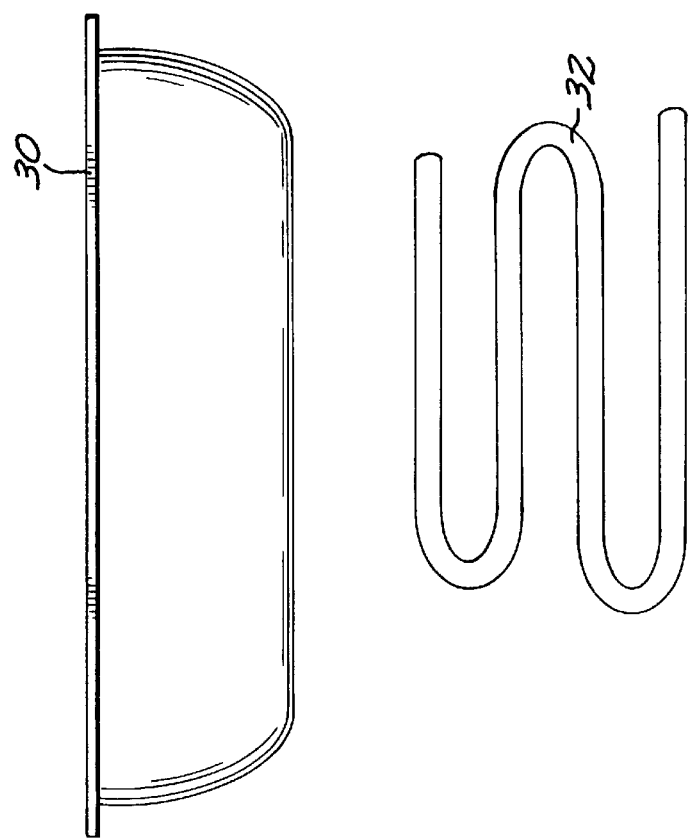
FIG. 1 is a cross-sectional view of the irrigation kit of the present invention.
Figure 1:
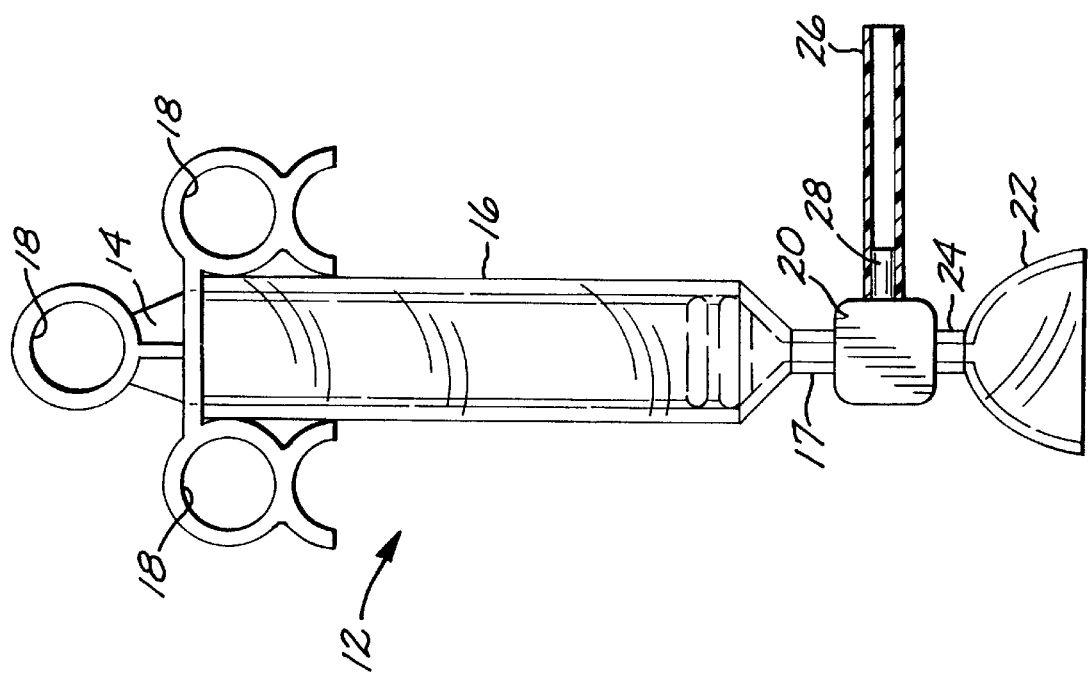

FIG. 1 is a cross-sectional view of the components of the kit including syringe assembly 12. A plunger 14 slideably received within a syringe 16 controls the flow of fluid. The three finger configuration 18 allows substantial forces to be applied to both compress as well as extend the plunger with only one hand. A two-way check valve 20 is fitted to the access port 17 at the distal end of the syringe. A splashback shield 22 is optionally fitted to its discharge port 24 while a short fill stem 26 is fitted to its fill port 28. The valve is configured to only allow fluid to be drawn in through the fill port i.e. fill stem, upon extension of the plunger. Conversely, the configuration only allows fluid to be expelled from the syringe through the discharge port upon compression of the plunger. An additional component of the irrigation kit is the open-faced basin 30 from which irrigant is repeatedly drawn. The supply of irrigant can thereby be positioned in close proximity to the wound while the large surface area of fluid contained therein provides easy access thereto. An absorbent pad 32 may be included in the kit for absorbing run off from the irrigated wound.

In use, saline solution 34 from for example, a screw-top bottle is poured directly into the basin 30. This immediately provides an advantage over the previously used IV bag systems in that bottled saline is somewhat less expensive than IV saline and in view of the fact that saline not poured from the bottle can be saved for later use. This is in contrast to the IV bag systems wherein once an IV bag is pierced, its entire contents must be used or discarded. Since hospitals typically stock 1000 cc IV bags, a substantial portion is discarded.

Once filled, the basin is positioned as close to the wound being treated as possible while the absorbent pad 32 is positioned therebelow so as to absorb runoff. As is shown in FIG. 2, the fill stem 26 is then simply dipped into the irrigant 34 while the plunger 14 is withdrawn in order to fill the syringe 16. Due to the short length of the fill stem, virtually no priming is necessary and the device is immediately ready for use. Compression of the plunger 14 causes the saline solution to be expelled while the splashback shield 22 serves to confine the irrigant to the wound. Repetition of the fill and expulsion cycle can be accomplished very quickly as the large surface area that the irrigant assumes within the basin obviates the need to pay close attention to accessing the fluid. It is thereby possible for the user to stay focused on the wound while refilling the syringe. Additionally, the short length of the fill stem affords no appreciable resistance to the flow of fluid therethrough. In fact, the flow rate through the 3" fill stem is increased by a factor of 24 when compared to the use of 6 feet of tubing that is typically used to interconnect an IV bag with the syringe. Delivery of the nominal 250 cc amount of saline at about 8–12 psi, can thereby be accomplished in as little as 90 seconds using a 10 cc syringe. Additionally, there is no need to be mindful of the many feet of tubing typically associated with IV bag systems to thereby obviate concerns of entanglement, kinking, interference and repositioning as well as maintaining the supply bag in a properly elevated position.

While a particular form of the invention has been illustrated and described, it will also be apparent tp those skilled in the art that various modifications can be made without departing from the spirit and scope of the invention. Accordingly, it is not intended that the invention be limited except by the appended claims.

What is claimed:

1. A wound irrigation kit, comprising:
   a syringe, including a plunger for varying its interior volume and an access port in fluid communication with said interior volume;
   a two-way check valve having a discharge port and an intake port wherein said discharge port is set into exclusive fluid communication with said access port while fluid is discharged from said syringe and wherein said intake port is set into exclusive fluid communication with said access port while said syringe is filled with fluid;
   a short fill stem extending from said intake port; and
   an open-faced basin for holding a supply of irrigant and availing the surface of said irrigant for access by said fill stem.

2. The wound irrigation kit of claim 1 further comprising a splashback shield in fluid communication with said discharge port.

3. The wound irrigation kit of claim 1 further comprising an absorbent underpad for absorbing runoff from a wound being irrigated.

4. The wound irrigation kit of claim 1 wherein said syringe holds a maximum volume of 10 cc and wherein said fill stem is 3" long.

5. A wound irrigation device comprising:
   a syringe, including a plunger for varying its interior volume and an access port in fluid communication with said interior volume;
   a two-way check valve having a discharge port and an intake port wherein said discharge port is set into exclusive fluid communication with said access port while fluid is discharged from said syringe and wherein said intake port is set into exclusive fluid communication with said access port while said syringe is filled with fluid; and a fill stem substantially shorter than said syringe extending from said intake port.

6. The wound irrigation device of claim 5 comprising a splashback shield in fluid communication with said discharge port.

7. A method for irrigating a wound, comprising the steps of:

pouring a quantity of irrigant into a open-faced basin;

positioning said basin as close as possible to the wound to be irrigated;

providing a syringe fitted with a two-way check valve that limits the flow of fluid into said syringe via a fill stem and the discharge of fluid from said syringe via a discharge port;

dipping said fill stem into said irrigant while filling said syringe;

positioning said discharge port above said wound to be irrigated while discharging said syringe; and repeating said filling and discharging steps as often as required.

8. The method of claim 5 further comprising the step of fitting a splashback shield to said discharge port.

* * * * *